United States Patent [19]

LePage

[11] 4,359,323

[45] Nov. 16, 1982

[54] SINGLE PUMP LIQUID CHROMATOGRAPH ANALYTICAL SYSTEM FOR AMINES

[75] Inventor: James N. LePage, Hudson, N.H.

[73] Assignee: W. R. Grace & Co., New York, N.Y.

[21] Appl. No.: 202,628

[22] Filed: Oct. 31, 1980

[51] Int. Cl.$^3$ ............................................. G01N 31/08
[52] U.S. Cl. .................................... 23/230 M; 422/70
[58] Field of Search ....................... 23/230 R, 230 M; 422/70; 73/61.1 C

[56] References Cited

U.S. PATENT DOCUMENTS

| | | | |
|---|---|---|---|
| 3,923,460 | 12/1975 | Parrott et al. ......................... | 422/70 |
| 4,165,219 | 8/1979 | Huber .................................... | 422/70 |
| 4,233,030 | 11/1980 | Twitchett et al. .................... | 422/70 |
| 4,278,438 | 7/1981 | Walraven ........................... | 23/230 R |

OTHER PUBLICATIONS

Chem. Abst., 93:26811k.
Mopper, *Borate Complex Ion Exchange Chromatography with Fluorimetric Detection for Determination of Saccharide*, Anal. Chem. 52, 2018 (1980).
Spackman et al., *Automatic Recording Apparatus for Use in Chromatography of Amino Acids*, Anal. Chem., 30, 1190, (1958).

*Primary Examiner*—Peter Chin
*Attorney, Agent, or Firm*—Michael J. McGreal

[57] ABSTRACT

This application discloses a liquid chromatography system which can be operated in a batch or a continuous mode. The system consists of the chromatographic column, a reaction column wherein the substances previously separated are reacted to form a readily detected compound and a loop to recycle the mobile phase for reuse. A prime feature of this system is having the mobile phase contain a reactant which upon reaction with an unknown produces a readily detectable compound. This system is very suitable for plant quality control operations and is of considerable value in analyzing compounds having primary amine functionality.

6 Claims, 3 Drawing Figures

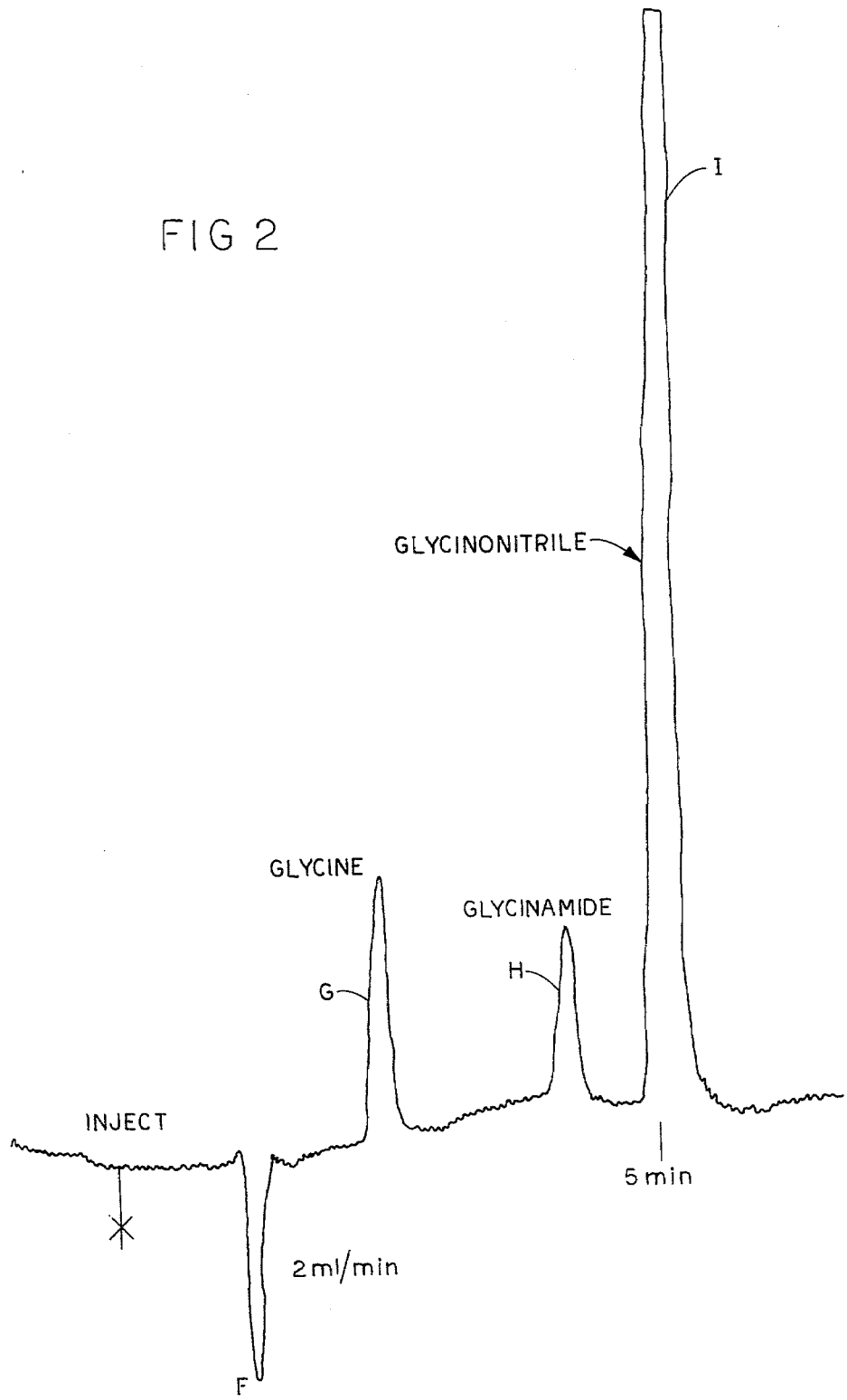

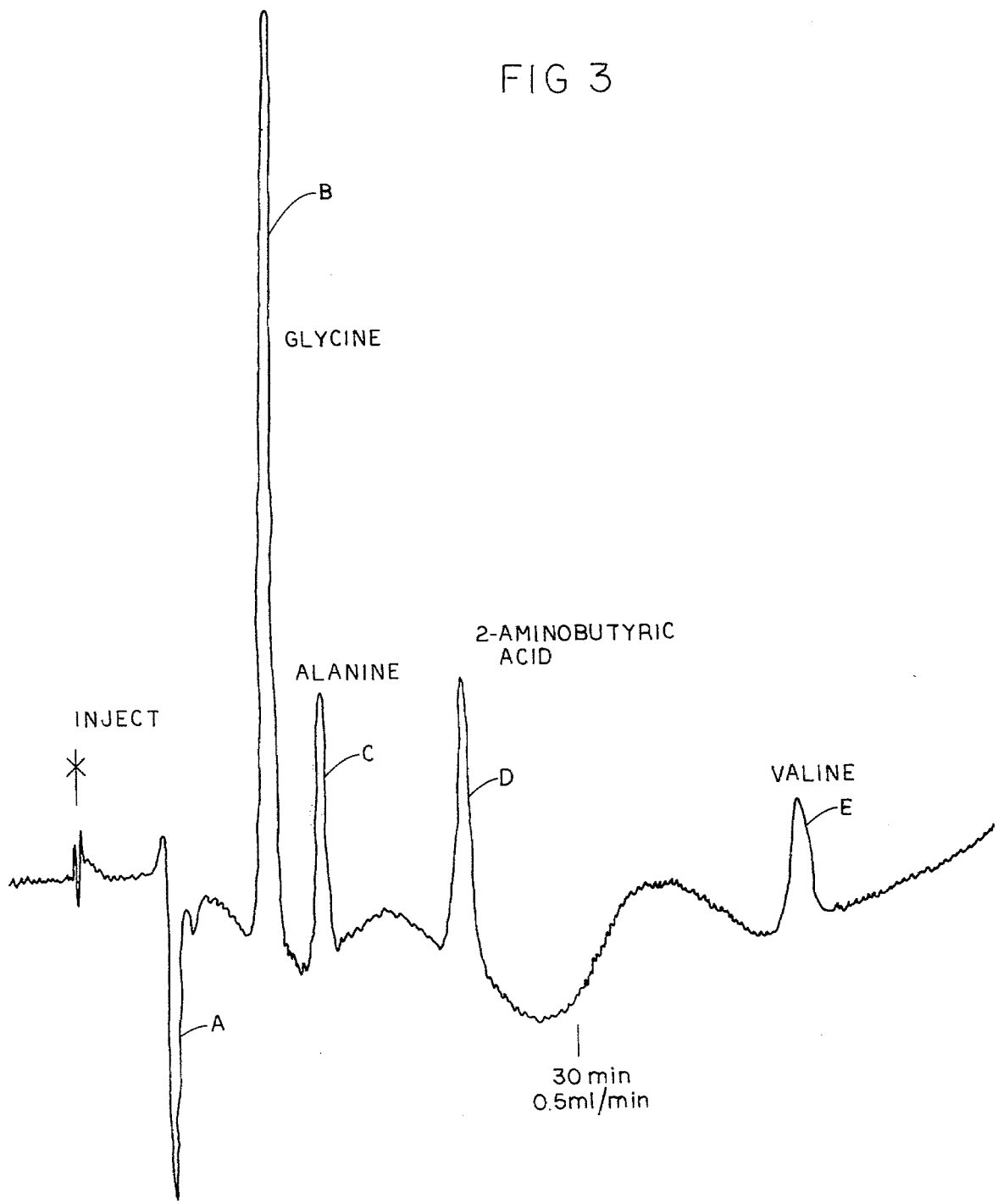

SINGLE PUMP LIQUID CHROMATOGRAPH ANALYTICAL SYSTEM FOR AMINES

This invention relates to a system for the liquid chromatographic analysis of amines which can be easily reacted subsequent to separation to produce a further substance which is readily detectable. More particularly, this invention relates to a system which can be used in the detection of compounds having a primary amine functionality at trace levels by using a mobile phase which contains as a component the substance which is to be reacted with the unknown compound which has primary amine functionality in order to produce a compound which is readily detectable photometrically or otherwise.

Liquid chromatography is a well-known analytical technique. It operates on the basis that an adsorbent will preferentially adsorb one substance to a greater extent than another substance. Therefore, as two or more components of a liquid advance along a column containing an adsorbent, either through gravity or by means of a pump, the adsorbent will adsorb each component, but the degree of attraction for each substance will differ. The net result is that the substance for which the adsorbent has the greater attraction will remain in the column longer than the substances for which it has a lesser attraction yielding a separation of these materials, one from the other. Each of the substances for which the adsorbent has an attraction leaves the chromatographic column at different intervals, and can then be analyzed qualitatively and quantitatively by various techniques. One convenient technique for analyzing trace amounts of amines, amino acids, and other compounds having amine functionality (contains a primary amine group) is to react substances with a reactant to yield a reaction product which can be analyzed photometrically.

The present system consists of a single pump liquid chromatographic system which can conveniently analyze on a batch or continuous basis trace amounts of amines, amino acids, and other compounds containing primary amine groups. The primary and most significant feature of this system consists of using as the liquid mobile phase a combination of an elutriant and a substance which reacts with the amine functionality to produce a compound which can be detected photometrically. That is, the mobile phase will contain a compound which will react with an amine group to produce a readily detectable compound. Besides providing excellent analytical results this process as a result of the mobile phase containing the reactant only requires a single pump for complete operation. This mobile phase is continuously pumped at a constant volume through the chromatographic column with the substances to be analyzed being introduced into the mobile phase at a point prior to the point that the mobile phase enters the chromatographic column. Within the chromatographic column the unknown substances are successively adsorbed and desorbed as they move through the column. The substance which is least attracted by the adsorbent exits the column in the mobile phase first and then enters a reaction column where, under the application of heat or radiant energy, such as ultraviolet, it reacts with the reactant component of the mobile phase to produce a compound which is easily detectable by photometric or other means. In the preferred embodiment of this application, this compound is easily photometrically analyzed and is flowed along with the mobile phase to a photometer after passing through the reaction column. The photometric detector conveniently has a strip chart recorder readout and by scanning certain wavelengths quantitatively provides a record of the substance being detected.

After the photometric detector the mobile phase which contains the reaction product can be recycled for use in subsequent analyses. In many instances this mobile phase can be reused since only trace amounts of materials are being analyzed with levels of the reaction products in the recycled mobile phase being very low and can be automatically compensated for by the photometer. Further, the use of a large reservoir of mobile phase serves to further dilute the levels of reaction product in a recycled mobile phase.

A prime and significant discovery leading to this system is that the mobile phase can contain the reactant prior to the injection of the unknown sample and prior to passage through the chromatography column. In any technique of this general nature up to this time the reactant was not introduced until after the chromatography separation column. These techniques, however, require the use of a second pump. Apparently, those in the prior art have been unduly concerned with interference by the reactant with the various unknowns within the separation column.

This invention will be described more fully with reference to the drawings which form a part of this specification. These drawings are as follows:

FIG. 2 is a segment from a strip chart recording showing the analysis of glycine, glycinamide, and glycinonitrile.

FIG. 3 is a segment from a strip chart recording showing the analysis of glycine, alanine, 2-aminobutyric acid, and valine.

Figure 1:
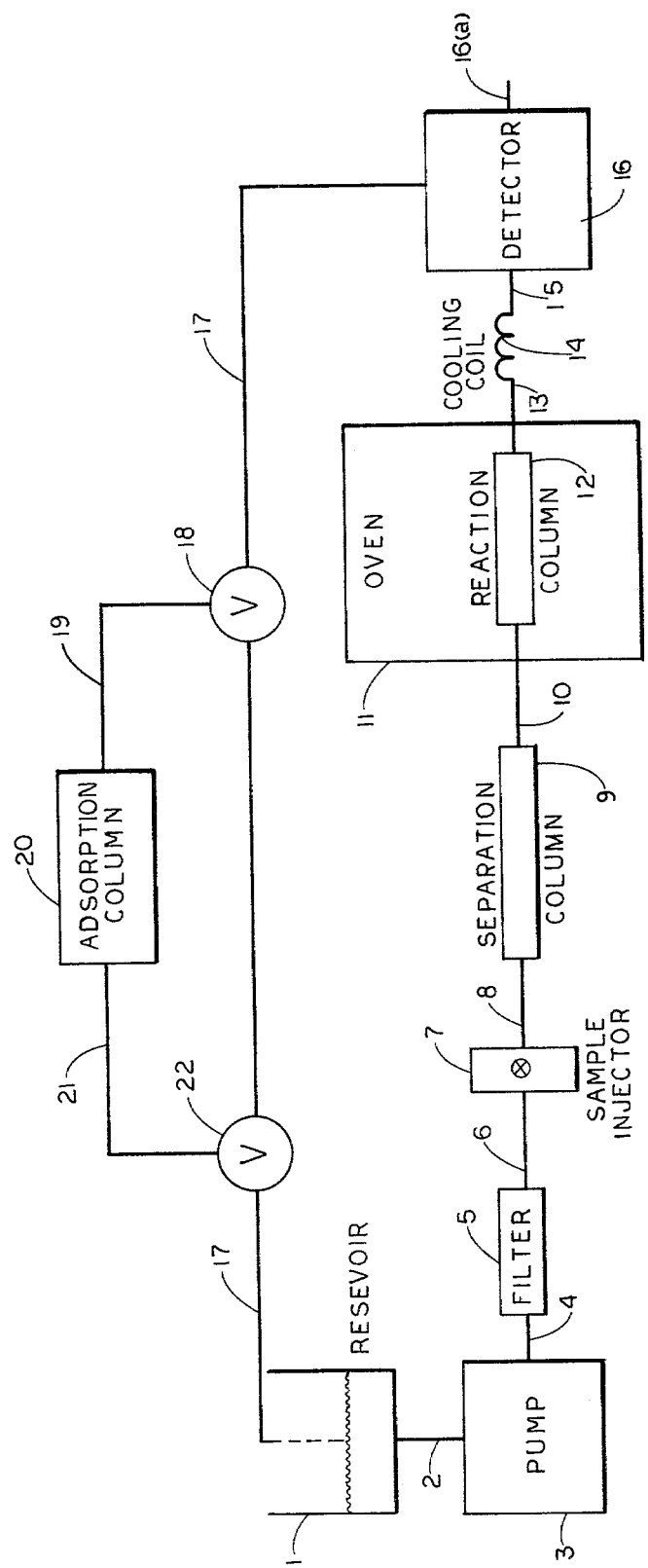
FIG. 1 is a schematic of the present system showing each of the components and conduits.

This analytical system will now be described in detail with reference to the drawings. In FIG. 1, the reservoir for the liquid mobile phase is designated 1 with conduit 2 delivering mobile phase from the reservoir to the pump 3. This pump is of a type to deliver a constant flow of mobile phase through the system. This is the only pump required in this system. Outlet conduit 4 from the pump delivers mobile phase to the in-line filter 5 which is an optional item in the system. That is, a filter although desirable, is not required in the system. Assuming a filter being in the system, conduit 6 delivers the mobile phase from the filter to the sample injector 7. It is at this point that the unknown substances are added to the mobile phase.

The unknown substances which are added to the mobile phase may be solids or liquids, but are usually liquids. If solids, they must be readily soluble in the mobile phase. The mobile phase, itself, consists of one or more elutriant liquids and a material which, upon the application of energy, is capable of reacting with the unknown substances. These components of the mobile phase are soluble, one in the other. Therefore, this mobile phase functions partially as a carrier for the substances to be analyzed and partially as a reactant. As a reactant, a part of the mobile phase is reactive with the unknown substances upon the application of heat or other energy to yield a compound which is readily detectable photometrically or via some other commonly used technique.

After leaving sample injection 7, the mobile phase now containing the unknown sample, flows through conduit 8 to chromatography column 9. This is a liquid chromatography column which contains an adsorbent which has an attractive affinity for the class of compounds which are to be analyzed. As the mobile phase and the sample are continuously adsorbed and desorbed, each to varying degrees. The components of the sample which are least adsorbed in the column will exit the column first, with the remaining components exiting the column at later intervals, depending on their adsorptivity. The most highly adsorbed component will exit the column last. As a result of these multiple adsorption-desorptions, the components of the sample are separated into discrete regions in the flowing mobile phase. This mobile phase exits the separation column through conduit 10, and flows into reaction column 12. In the embodiment in FIG. 1, this reaction column is contained within oven 11 since the separated components of the sample and the reactive component in this embodiment can be reacted at an elevated temperature to form a compound which can be easily detected photometrically. This reaction column may contain a catalyst and/or it may be packed with glass, wool, or the like to promote good lateral mixing of the mobile phase so as not to broaden the previously separated bands. The oven is replaced with a UV or other radiant energy chamber for reactions which are promoted by other types of energy.

The mobile phase, which now contains the more readily detectable reaction product of an unknown and the reactive component of the mobile phase, exits the reaction column via conduit 13 and passes through optional cooling coil 14. Such a cooling coil would not be necessary if UV or some other radiant energy were used. After leaving the cooling coil, the mobile phase flows through conduit 15 and into the detector 16. In a preferred embodiment, this detector is a scanning photometer. That is, it is continuously scanning a set light frequency range with the adsorption of light energy at a particular frequency directly set out on a strip chart recorder. Since the frequency of the light energy which is adsorbed by compounds which are found by the class of compounds being analyzed is known, the output from the strip chart recorder can quickly be interpreted to provide the desired qualitative and quantitative data. The mobile phase then exits the detector and in the usual case will be discarded through conduit 16($a$). However, when it is desired to operate the system continuously the mobile phase will pass through conduit 17 and is flowed to reservoir 1, or in the alternative, may undergo a treatment to remove some or all of the compounds which were formed in the reaction column with the unknown substances. This full or partial purification can be done in series or parallel with the remainder of the system. In FIG. 1, it is shown in parallel with valves 18 and 22 being adjustable to flow the mobile phase at this point through conduit 19, an adsorption column 20, and conduit 21. It is understood that in place of the adsorption column any other means whereby the mobile phase can be purified can be used. If an adsorption column is used, adsorbent grades of carbon are useful.

FIGS. 2 and 3 set forth excerpts from the strip chart recordings of actual analyses of samples of compounds containing primary amino groups.

FIG. 3 illustrates the use of the system of FIG. 1 for the analysis of an unknown sample which contains various amino acids. In this embodiment, the mobile phase consists of sodium dodecyl sulfate, methanol, water and sodium phosphate to adjust the pH to below 2.5. The reactant component is perinaphthindan-2,3,4-trione hydrate. The mobile phase was pumped at 0.5 ml/min. and the sample injected at the rate of 0.5 ml/min. The chromatography column was a reverse phase column maintained at 25° C. and the oven 11 was maintained at 105° C. Each of the separated amino acids reacts with the peri-naphthindan-2,3,4-trione hydrate in the reaction tube 12, in oven 11. The objective of this run was to separate these amino acids, one from the other, and to convert them to a form where they can be detected photometrically. The photometer was set to scan frequencies in the range of 380 nm. FIG. 3 sets forth the photometer output with the inverted peak A representing the holdup or dead volume of the system. Peaks B, C, D, and E represent glycine, alanine, 2-aminobutyric acid, and valine, respectively. The integrated area under each of these peaks gives the quantitative amount of the particular amino acid in the sample.

FIG. 2 illustrates the use of the system of FIG. 1 for the analysis of a sample which contains amines. The mobile phase contains sodium dodecyl sulfate, methanol, water and sodium phosphate to adjust the pH to 2.5, which functions as the elutriant and peri-naphthindan-2,3,4-trione hydrate which functions as the reactant component. The sample to be analyzed contains glycinamide, glycinonitrile, and glycine. The objective in this instance is to detect the glycine and glycinamide in this mixture. The mobile phase is pumped through the system at the rate of 2 ml/min. The chromatographic column is of the reverse phase type and is maintained at 25° C. The oven which contains the reaction column was maintained at 105° C., and is packed with non-porous glass beads. The above components of the mixture were separated in the separation column 9, and were reacted in the reaction column 12 with the peri-naphthindan-2,3,4-trione hydrate of the mobile phase to yield di-hydroxy peri-naphthindenone as the principal reaction product. The compound which absorbs light energy in the frequency range of 380 nm was flowed with the mobile phase to the photometric detector which was set to scan this part of the visible spectrum. With particular reference to FIG. 2, the inverted peak F represents the dead volume of the system. G and H are the glycine and glycinamide peaks with peak I showing the presence of glycinonitrile. The area under the glycine and glycinamide peaks represents the relative amount of each of these materials present in the sample.

This present system is particularly adaptable for quality control analyses since a large number of runs can be made prior to shutting down the system for cleaning and replacement of any of the adsorbents or of the mobile phase. When the device is used for a multiple number of analyses, it is desirable to flow a small amount of the mobile phase directly from the reservoir to the photometric detector for use as a reference. This will preclude base line drift of the curves of the multiple analyses are being performed.

Although this invention has been described using peri-naphthindan-2,3,4-trione hydrate as the reactance, other substances such as ninhydrin-hydrindantin can be used for primary and secondary amines. In this latter case, a higher pH and a different wavelength would be used. When peri-naphthindan-2,3,4-trione hydrate is used, the reaction product is di-hydroxy peri-naphthindenone.

Those skilled in the art will devise other adaptations of this sytem. However, all such adaptations which use the concept of adding a reactive component to the mobile phase prior to separation in a liquid chromatography column for the purposes of detection, would be within the scope of the present invention.

What I claim is:

1. A method for analyzing solutions containing unknown components having amine functionality by means of liquid chromatography comprising:
   (a) providing a mobile phase reservoir, at least one component of the mobile phase in said reservoir being a reactive component selected from the group consisting of ninhydrin-hydrindantin and peri-naphthindan-2,3,4-trione hydrate;
   (b) adding a solution containing at least one unknown component having amine functionality to said mobile phase to form a mixture;
   (c) passing said mixture through a liquid chromatography column wherein the unknown components are selectively adsorbed to differing extents thereby providing at the exit end thereof a mobile phase containing varying amounts of particular unknown components;
   (d) contacting the mobile phase solution which exits said liquid chromatography column with radiant energy to react at least one of the separated unknown components with the reactive component of said mobile phase to form one or more reaction products;
   (e) determining the identity of at least one of the unknown components by means of detecting a particular and known characteristic of the reaction product; and
   (f) directly flowing the modile phase containing said one or more reaction products to said mobile phase reservoir.

2. A method as in claim 1, wherein the identity of the reaction product of an unknown component and the reactive component of said mobile phase is determined by means of detecting the wavelength of radiation absorbed by said reaction product.

3. A method as in claim 2, wherein at least one of the unknown components is selected from the group consisting of amines and amino acids.

4. A method for analyzing solutions containing unknown components having amine functionality by means of liquid chromatography comprising:
   (a) providing a mobile phase reservoir, at least one component of the mobile phase in said reservoir being reactive with at least one of the unknown components of a solution having amine functionality;
   (b) adding a solution containing the unknown components to said mobile phase to form a mixture;
   (c) passing said mixture through a liquid chromatography column wherein the unknown components are selectively adsorbed to differing extents thereby providing at the exit end thereof a mobile phase containing varying amounts of particular unknown components;
   (d) contacting the mobile phase solution which exits said liquid chromatography column with radiant energy to react at least one of the separated unknown components with the reactive component of said mobile phase to form one or more reaction products;
   (e) determining the identity of at least one of the unknown components by means of detecting a particular and known characteristic of the reaction product; and
   (f) directly flowing the mobile phase containing said one or more reaction products to said mobile phase reservoir.

5. A method as in claim 4, wherein the identity of the reaction product of an unknown component and the reactive component is determined by means of detecting the wavelength of radiation adsorbed by said reaction product.

6. A method as in claim 5, wherein at least one of the unknown components is selected from the group consisting of amines and amino acids.

* * * * *